United States Patent [19]

Sobel

[11] 4,041,101
[45] Aug. 9, 1977

[54] HF ALKYLATION PROCESS WITH ADDITION OF ACID REGENARATOR BOTTOMS TO THE RECYCLE ISOPARAFFIN STREAM

[75] Inventor: Jay E. Sobel, Highland Park, Ill.

[73] Assignee: UOP Inc., Des Plaines, Ill.

[21] Appl. No.: 637,444

[22] Filed: Dec. 3, 1975

[51] Int. Cl.² ............................................. C07C 3/54
[52] U.S. Cl. ............................................. 260/683.51
[58] Field of Search ...................... 260/683.48, 683.51, 260/683.49

[56] References Cited

U.S. PATENT DOCUMENTS

| | | | |
|---|---|---|---|
| 3,408,419 | 10/1968 | Herber et al. .................... | 260/683.48 |
| 3,755,485 | 8/1973 | Sobel ............................... | 260/683.51 |
| 3,825,617 | 7/1974 | Hervert ........................... | 260/683.48 |
| 3,928,486 | 12/1975 | Sobel ............................... | 260/683.49 |
| 3,948,603 | 4/1976 | Zabransky ....................... | 260/683.48 |

*Primary Examiner*—George Crasanakis
*Attorney, Agent, or Firm*—James R. Hoatson, Jr.; Thomas K. McBride; William H. Page, II

[57] ABSTRACT

A process is disclosed for alkylating an isoparaffin with an olefin using HF acid. Unreacted isoparaffin, usually isobutane, is recycled. The presence of a free HF acid phase in isobutane recycled to the reaction zone can be tolerated because the deleterious effects of the HF acid are attenuated by the addition of an organic diluent. A preferred source of organic diluent is the bottoms fraction from the HF acid regenerator.

4 Claims, 1 Drawing Figure

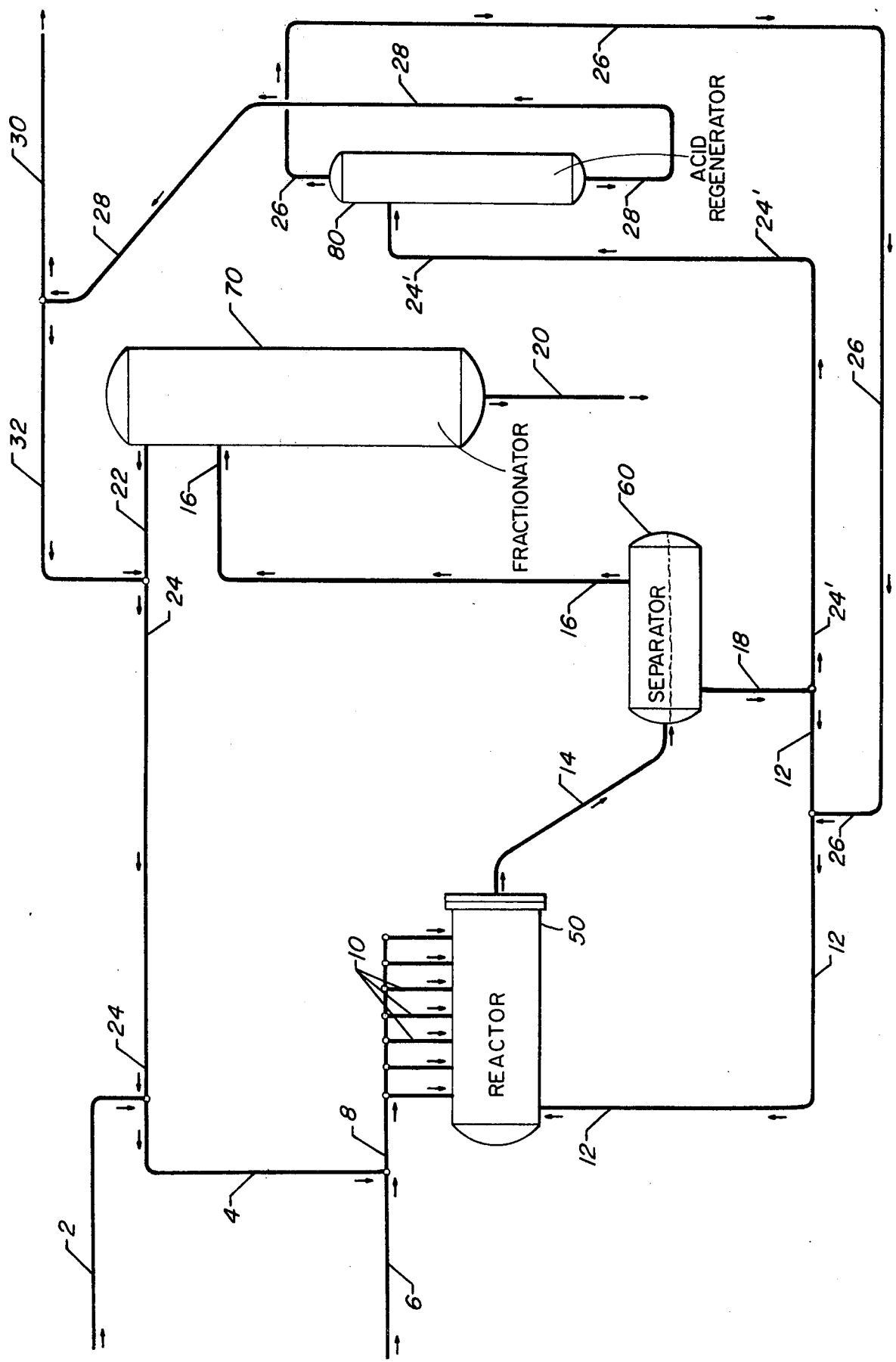

HF ALKYLATION PROCESS WITH ADDITION OF ACID REGENARATOR BOTTOMS TO THE RECYCLE ISOPARAFFIN STREAM

BACKGROUND OF THE INVENTION

The invention relates to a process for alkylating an isoparaffin with an olefin using HF acid catalyst.

The HF alkylation process itself is well known in the art. Work in this process began during World War II, and has continued today. Recent patents showing the trend of development of the HF alkylation process are U.S. Pat. No. 3,560,587 (Class 260-683.48), U.S. Pat. No. 3,755,485 (Class 260-671R) and U.S. Pat. No. 3,825,617 (Class 260-683.48) and U.S. Pat. 3,845,158 (Class No. 260-683.49), the teachings of which are incorporated by reference herein.

U.S. Pat. No. 3,560,587 shows a modern reactor design wherein olefin, isobutane, and acid are contacted in a reactor containing multiple feed injection points. The reactor contains provisions for cooling of the reaction mass. A reaction soaker is used. In this design, the olefin and isobutane reactants contact one another in the piping leading up to the reactor vessel.

In U.S. Pat. No. 3,755,485, the advantages of operating the alkylation process in the presence of a unique organic diluent, or catalyst diluent, formed by reacting a terpene with an alkylation catalyst, are disclosed. This patent is cited to show some of the recent work done with organic diluents. The function of this organic diluent is to modify or attenuate the catalytic activity of the HF acid phase in the reaction zone.

In U.S. Pat. No. 3,825,617, the hyperactive character of virgin HF acid catalyst is recognized. The invention disclosed in this patent is a way to "startup" a unit by quickly generating an organic diluent, in situ, by maintaining special conditions in the reaction zone, including low temperatures and low amount of isobutane recycle relative to olefin reactant. Again, the teaching is directed toward attenuating the activity of the HF acid in the reaction zone.

In my U.S. Pat. No. 3,845,158, I disclosed that use of organic diluents to attenuate the activity of the HF acid catalyst is also useful when applied to a fluorination step. The fluorination step is performed to improve the subsequent alkylation reaction.

Other examples of the use or organic diluents may be found in U.S. Pat. No. 3,408,419 (Class 260-683.51) and in U.S. Pat. No. 3,538,183 (Class 260-683.48), the teachings of which are incorporated by reference.

In all of these references the patentees attempt to modify the action of acid in the reaction zone. There is no explicit recognition of the problems that a refiner encounters if his recycle isobutane contains a free HF acid phase suspended therein. There is a problem, because the acid contained in the recycle isobutane stream is exceedingly pure, having been recovered as an overhead fraction in at least one fractionating column. The organic diluent normally present in the HF acid in the reaction zone, is no longer present in the acid phase because the fractionation step separated the acid from its diluent.

The way refiners have attempted to solve this problem in the past is to provide yet another stage of fractionation to remove HF acid from recycle isobutane. Another altenative is to redesign the existing HF alkylation product fractionation facilities to insure that no free HF acid phase will form in the recycle isobutane.

Many times it is not possible to modify an existing HF alkylation unit fractionation facilities without great capital expense. In the instances when modification of fractionation facilities is not economically justifiable, refiners have attempted to find other ways of ameliorating the bad effects of a free HF acid phase in recycle isobutane. In U.S. Pat. No. 3,775,510 the teachings of which are incorporated by reference, a recycle isobutane phase is cooled and passed to a two phase separator. The HF acid phase is removed and the recycle isobutane charged to the reactor. This will remove most of the dissolved HF acid in this stream. Such an approach adds significantly to the capital expense of a unit, and also consumes much utilities, and has not found great favor in the art.

Another attempt to solve this problem was disclosed in U.S. Pat. No. 3,818,938 (Class 137/604) the teachings of which are incorporated by reference. The patentee attempted to prevent the occurrence of undesirable side reactions between acid, in a recycle isoparaffin stream, and olefin feedstock, by providing a feed nozzle which would promote intense mixing of the feed components and minimize the chance that olefins would contact pockets of acid before dispersed in isobutane. Although the apparatus disclosed in this patent was an improvement over the prior processes and an improvement which could be incorporated into many existing units, without great incremental expense, it was an attempt to mechanically eliminate a problem caused by the chemical activity of the free acid phase.

Because none of the known methods of minimizing the deleterious effects of a free HF acid phase in the recycle isobutane stream charged to an HF alkylation reactor were completely satisfactory, for some units, work has continued to try to find a better way to operate the many HF alkylation units in existence today. With the trends toward unleaded gasoline in many countries in the world, refiners have been striving to improve the performance of all of their processing units. Of crucial importance to a refiner's effect to produce great volumes of high octane unleaded gasoline is the operation of the HF alkylation unit.

BRIEF SUMMARY OF THE INVENTION

In one embodiment, the present invention provides a process for alkylating an olefin with an isoparaffin in the presence of HF acid catalyst in a reaction zone wherein the amount of isoparaffin is in excess of that required to react with the olefin, unreacted isoparaffin is recovered by fractionation from alkylate product, at least a portion of unreacted isoparaffin is recycled to the reaction zone, and wherein there is present in the recycle isoparaffin stream HF acid of high activity, the improvement comprising adding to the recycle isoparaffin stream an organic diluent thereby attenuating the activity of the HF acid in the recycle isoparaffin.

In a more limited embodiment, the present invention provides a process for alkylating an olefin with an isoparaffin in the presence of HF acid catalyst in a reaction zone wherein the amount of isoparaffin is in excess of that required to react with the olefin, unreacted isoparaffin is recovered by fractionation from alkylate product, at least a portion of unreacted isoparaffin is recycled to the reaction zone, and wherein there is present in the recycle isoparaffin stream a HF acid of high activity, and wherein at least a portion of the HF acid catalyst used in the reaction zone is removed from the process for regeneration in an HF acid regenerator fractionator, and a stream of organic diluent is recovered as a bottoms fraction from said fractionator, the improvement comprising adding at least a portion of said organic diluent to the recycle isoparaffin stream thereby attenuating the activity of the HF acid contained in the recycle isoparaffin.

BRIEF DESCRIPTION OF THE DRAWING

The attached drawing is a schematic representation of one embodiment of the present invention wherein the HF acid regenerator is the source of organic diluent for free acid contained in the isobutane recycle.

DETAILED DESCRIPTION

Recycle isobutane from line 24 is admixed with fresh olefin feed in line 2 and the mixture charged via line 4 to line 8. Fresh isoparaffin feed is charged to the process via line 6. Line 8, containing a mixture of fresh and recycle isoparaffin and fresh olefin, passes the hydrocarbon feed to reactor 50 via multiple distributors 10. Reactor 50 has provisions for multiple injection of feed, which produces a higher product octane. Not shown are provisions for cooling the reaction mass and multiple internal baffles which promote mixing of hydrocarbon and acid reactants within reactor 50. The particular design of the reactor is not a part of my invention, and the design of such reactors is well known to those skilled in the HF alkylation arts. HF acid is charged to reactor 50 via line 12.

Effluent from reactor 50 is removed via line 14 and charged to separator 60. Not shown in between reactor 50 and separator 60 is a reaction soaker, a conventional vessel which insures that the desired alkylation reactions are completed, and gives any alkyl fluorides formed in reactor 50 sufficient time to break down into alkylate and HF acid. In separator 60, a hydrocarbon phase is recovered overhead via line 16 while an acid phase is recovered as a bottoms fraction via line 18 and recycled to reactor 50 via line 12. The design of separator 60 is conventional and forms no part of my invention.

A small slip stream of the acid phase recovered in line 18 is charged via line 24' to acid regenerator 80. This regenerator is a conventional device which separates HF acid from impurities present therein via fractionation. Regenerated acid is recovered overhead from this vessel via line 26 and charged back to the reaction zone via line 12. The bottoms fraction from the acid regenerator is recovered via line 28 and the bulk of it sent to disposal facilities via line 30. The remainder of the bottoms fraction from the acid regenerator is charged via line 32 for mixing with isobutane recycled to the reaction zone.

The hydrocarbon phase recovered from separator 60 is charged via line 16 into product fractionation facility 70. A high octane alkylate product is recovered as a bottoms fraction via line 20. Unreacted isobutanes are removed via line 22 for recycle to the reaction zone. There is a free HF acid phase because the isobutane is recovered as an overhead fraction, and any HF acid dissolved or entrained in hydrocarbon in line 16 will also be recovered as an overhead fraction.

In the embodiment shown, the essence of the present invention is line 32. Use of the HF acid regenerator as a convenient and inexpensive source of O.D., organic diluent, to attenuate the acid strength of free HF acid contained in the recycle isobutane stream results in significantly improved operation. Although it is much preferred to use the bottoms fraction from the acid regenerator as the source of organic diluent for recycled isobutane, any other source of organic diluent may also be used. Of course, the operation of the acid regenerator may be intermittent with excess production of bottoms material stored in a tank for eventual use in attenuating the acid strength in the recycle isobutane stream.

In some installations it may be desirable to provide even further fractionation facilities to separate the organic diluent from any other materials which may be present in the bottoms fraction recovered from the HF acid regenerator. Similarly, it may be desirable to use only a light fraction, or heavy fraction, of the organic diluent recovered from the material in line 28.

EXAMPLE

A series of alkylation experiments were carried out with isobutane and a mixture of $C_4$ olefins. The reaction conditions were:

Temperature: 68° F
Isobutane/Olefin ~ 12/1 molar
Olefin Feed ~ 40% Isobutane, 37% 2-butene, 23% 1-butene
Alkylation Acid: $HF/OD/H_2O$ ~ 89/10/1
Residence Time: 10 minutes
Acid/Hydrocarbon: 3/2 volume The differences between the runs were in the composition of the isobutane used to simulate isobutane recycle. These data and the results obtained are summarized in the following table.

| | | | | | |
|---|---|---|---|---|---|
| % HF In Isobutane (wt) | None | 4.85 | 4.0 | 4.35 | 4.35 |
| % Organic Diluent In Isobutane (wt) | None | None | 4.0 | 0.49 | 0.49 |
| Alkylate | | | | | |
| RON | 97.2 | 95.2 | 97.0 | 96.7 | 97.3 |
| MON | 95.4 | 94.1 | 94.0 | 94.0 | 93.6 |
| TMP/DMH | 7.11 | 5.81 | 7.10 | 6.59 | 6.88 |

The accuracy of the RON is ± 0.1 octane number, the accuracy of the MON is ± 0.5 octane number. This is due to the smaller sample used in the motor octane number determination.

These data clearly indicate the value of attenuating the acid in the isobutane recycle by adding organic diluent to the isobutane. The increase in RON + MON as well as the trimethyl pentane (TMP)/dimethyl hexane (DMH) ratio both reflect the improved performance.

Accordingly, the practice of the present invention permits refiners to operate their existing HF alkylation units without fear that product octane number will decline if there is a free HF acid phase present in the recycle isobutane. For those units wherein the presence of free acids occurs only during upsets of the unit, the present invention may be practiced intermittently.

The amount of organic diluent added should be enough to attenuate the acid present in the recycle isobutane stream. Based upon the amount of total HF acid (i.e., including dissolved and free liquid HF), the weight ratio or organic diluent to HF acid should be at least 1/19 to 1/1. Operation with less organic diluent than the minimum value given would not, it is believed, provide sufficient attenuating effect. Operation with ratios greater than the above specified maximum would not significantly improve the octane number of the alkylate, and would result in a significant increase in the flow rate to HF acid regenerator 80, without a corresponding benefit gained thereby.

I claim as my invention:

1. In a process for alkylating an olefin with an isoparaffin in the presence of HF acid catalyst in a reaction zone wherein the amount of isoparaffin is in excess of that required to react with the olefin, unreacted isoparaffin is recovered by fractionation from alkylate product, at least a portion of unreacted isoparaffin is recycled to the reaction zone, and wherein there is present in the recycle isoparaffin stream a HF acid of high activity and wherein at least a portion of the HF acid catalyst used in the reaction zone is removed from the process for regeneration in a HF acid regenerator fractionator and a stream of organic diluent is recovered as a bottoms fraction from said fractionator, the improvement comprising addition at least a portion of said organic diluent to the recycle isoparaffin stream thereby attenuating the activity of the HF acid contained in the recycle isoparaffin.

2. Improved process of claim 1 wherein the weight ratio of organic diluent to HF acid present in the recycle isoparaffin stream is 1/19 to 1/1.

3. Improved process of claim 1 wherein the isoparaffin is isobutane.

4. Improved process of claim 1 wherein the recycle isoparaffin stream contains both dissolved and free HF acid.

* * * * *